(12) United States Patent
Candelli et al.

(10) Patent No.: US 12,053,778 B2
(45) Date of Patent: *Aug. 6, 2024

(54) METHOD AND SYSTEM FOR STUDYING BIOLOGICAL CELLS

(71) Applicant: LUMICKS CA HOLDING B.V., Amsterdam (NL)

(72) Inventors: Andrea Candelli, Amsterdam (NL); Felix Oswald, Amsterdam (NL); Gerrit Sitters, Amsterdam (NL)

(73) Assignee: LUMICKS CA HOLDING B.V. (NL)

( * ) Notice: Subject to any disclaimer, the term of this patent is extended or adjusted under 35 U.S.C. 154(b) by 447 days.

This patent is subject to a terminal disclaimer.

(21) Appl. No.: 17/529,498

(22) Filed: Nov. 18, 2021

(65) Prior Publication Data

US 2022/0118453 A1   Apr. 21, 2022

Related U.S. Application Data

(63) Continuation of application No. 16/346,056, filed as application No. PCT/EP2017/078090 on Nov. 2, 2017, now Pat. No. 11,207,684.

(30) Foreign Application Priority Data

Nov. 2, 2016 (NL) .................................. 2017705

(51) Int. Cl.
*B01L 3/00* (2006.01)
*B01L 7/00* (2006.01)
(Continued)

(52) U.S. Cl.
CPC ..... *B01L 3/502761* (2013.01); *B01L 3/50273* (2013.01); *B01L 7/00* (2013.01);
(Continued)

(58) Field of Classification Search
CPC ..... B01L 2200/0652; B01L 2300/0663; B01L 2300/163; B01L 2300/1822;
(Continued)

(56) References Cited

U.S. PATENT DOCUMENTS 6,086,821 A   7/2000 Lee
6,589,727 B1  7/2003 Klenerman et al.
(Continued)

FOREIGN PATENT DOCUMENTS

CN   1347500 A   5/2002
CN   1582327 A   2/2005
(Continued)

OTHER PUBLICATIONS

Liu Ap, "Biophysical Tools for Cellular and Subcellular Mechanical Actuation of Cell Signaling", Biophysical Journal, Sep. 2016; vol. 111(6): pp. 1112-1118.
(Continued)

*Primary Examiner* — Jennifer Wecker
(74) *Attorney, Agent, or Firm* — Mendelsohn Dunleavy, P.C.

(57) ABSTRACT

A method of manipulating and/or investigating cellular bodies (9) is provided. The method comprises the steps of: providing a sample holder (3) comprising a holding space (5) for holding a fluid medium (11); providing a sample (7) comprising one or more cellular bodies (9) in a fluid medium (11) in the holding space (5); generating an acoustic wave in the holding space exerting a force (F) on the sample (7) in the holding space (5). The method further comprises providing the holding space (5) with a functionalised wall surface portion (17) to be contacted by the sample (7) and the sample (7) is in contact with the functionalised wall
(Continued)

surface portion (17) during at least part of the step of application of the acoustic wave. A system and a sample holder (3) are also provided.

16 Claims, 7 Drawing Sheets

(51) Int. Cl.
  *G01N 15/1429* (2024.01)
  *G01N 21/03* (2006.01)
  *G01N 21/17* (2006.01)
  *G01N 29/036* (2006.01)
  *G01N 29/22* (2006.01)
  *G01N 29/24* (2006.01)
  *G01N 29/34* (2006.01)
  *G01N 21/64* (2006.01)

(52) U.S. Cl.
  CPC ..... *G01N 15/1429* (2013.01); *G01N 21/0332* (2013.01); *G01N 29/036* (2013.01); *G01N 29/222* (2013.01); *G01N 29/2437* (2013.01); *G01N 29/2462* (2013.01); *G01N 29/346* (2013.01); *G01N 29/348* (2013.01); *B01L 2200/0652* (2013.01); *B01L 2300/0663* (2013.01); *B01L 2300/163* (2013.01); *B01L 2300/1822* (2013.01); *B01L 2400/0436* (2013.01); *G01N 2021/177* (2013.01); *G01N 21/6458* (2013.01); *G01N 2291/014* (2013.01); *G01N 2291/02466* (2013.01); *G01N 2291/02475* (2013.01); *G01N 2291/0255* (2013.01); *G01N 2291/0256* (2013.01); *G01N 2291/0257* (2013.01); *G01N 2291/02809* (2013.01); *G01N 2291/0423* (2013.01); *G01N 2291/0426* (2013.01)

(58) Field of Classification Search
  CPC ......... B01L 2400/0436; B01L 3/50273; B01L 3/502761; B01L 7/00; G01N 15/1023; G01N 15/1425; G01N 15/1429; G01N 15/1433; G01N 15/1484; G01N 2015/1006; G01N 2015/1027; G01N 2021/177; G01N 21/0332; G01N 21/6458; G01N 2291/014; G01N 2291/02466; G01N 2291/02475; G01N 2291/0255; G01N 2291/0256; G01N 2291/0257; G01N 2291/02809; G01N 2291/0423; G01N 2291/0426; G01N 29/022; G01N 29/036; G01N 29/222; G01N 29/2437; G01N 29/2462; G01N 29/346; G01N 29/348; G01N 33/5047; G01N 33/5076; G01N 33/5079; G01N 33/5082; G01N 33/54353
  See application file for complete search history.

(56) References Cited

U.S. PATENT DOCUMENTS

| | | | |
|---|---|---|---|
| 7,081,192 B1 | 7/2006 | Wang et al. | |
| 2003/0170613 A1 | 9/2003 | Straus | |
| 2005/0015001 A1* | 1/2005 | Lec | A61B 8/12 73/64.42 |
| 2007/0184433 A1 | 8/2007 | Tao et al. | |
| 2008/0108130 A1 | 5/2008 | Nakaminami et al. | |
| 2011/0207238 A1* | 8/2011 | Horii | B01L 3/502761 422/69 |
| 2013/0130884 A1 | 5/2013 | Wong et al. | |
| 2014/0099014 A1 | 4/2014 | Kii et al. | |
| 2014/0376816 A1 | 12/2014 | Lagae et al. | |
| 2016/0370266 A1 | 12/2016 | White et al. | |

FOREIGN PATENT DOCUMENTS

| | | |
|---|---|---|
| CN | 1920559 A | 2/2007 |
| CN | 101065671 A | 10/2007 |
| CN | 103025859 A | 4/2013 |
| CN | 103221529 A | 7/2013 |
| CN | 104136907 A | 11/2014 |
| CN | 104195028 A | 12/2014 |
| JP | 2006-526134 A | 11/2006 |
| WO | 02063280 A1 | 8/2002 |
| WO | 2004101730 A1 | 11/2004 |
| WO | 2011106384 A1 | 9/2011 |
| WO | 2011149526 A2 | 12/2011 |
| WO | 2014200341 A1 | 12/2014 |
| WO | 2015153816 A3 | 10/2015 |

OTHER PUBLICATIONS

Lee, Jungwoo et al., "Targeted cell immobilization by ultrasound microbeam", Biotechnology and Bioengineering; Jul. 2011; vol. 108(7); pp. 1643-1650.
Baresch, Diego et al., "Observation of a Single-Beam Gradient Force Acoustical Trap for Elastic Particles: Acoustical tweezers", Physics Review Letters vol. 116; Jan. 2016; p. 024301.
Marx, Vivien, "Biophysics: using sound to move cells"; Nature Methods vol. 12; Jan. 2015; p. 41-44.
Mulvana, Helen et al., "Ultrasound assisted particle and cell manipulation on-chip", Advanced Drug Delivery Reviews vol. 65; Nov. 2013; p. 1600-1610.
Lenshof, A. et al., "Acoustofluidics 5: Building microfluidic acoustic resonators."; Lab on a Chip vol. 12; 2012; p. 684-695.
Evander, M. et al., "Acoustofluidics 20: Applications in acoustic trapping."; Lab on a Chip vol. 12; 2012; p. 4667-4676.
EPO International Search Report and Written Opinion for application PCT/EP2017/078090 dated Mar. 29, 2019.
Siddique A K et al., "Use of frequency swept ultrasound to manipulate Nb2-11 live cells in a microfluidic channel"; Journal of the Korean Physical Society vol. 64 Issue 2; Jan. 2014; p. 226-231.
PCT Direct Letter for Dutch patent application NL2017705, dated Nov. 2, 2017, in response to International Type Search Report (SN 68425).
Zourob Mohammed et al., "An integrated metal clad leaky waveguide sensor for detection of bacteria." Analytical Chemistry vol. 77, Issue 1; 2005; p. 232-242.
Bhatta, D. et al., "Multiplexed detection of biological agents using optical microchip sensors", Optics and Photonics for Counterterrorism and Crime Fighting VI and Optical Materials in Defence Systems Technology VII, vol. 7838; Oct. 2010; p. 78380X.
Ding, X. et al., "On-chip manipulation of single microparticles, cells, and organisms using surface acoustic waves", Proceedings of the National Academy of Sciences, vol. 109, Issue 28; Jul. 2012; p. 11105-11109.
International Search Report and Written Opinion for the Dutch Priority Application 2 017 705 dated Aug. 9, 2017.
First Office Action for corresponding Chinese application No. 201780081915.1; dated Jun. 30, 2021 (32 pages) Machine Translation.
Notice of Reasons for Rejection for corresponding Japanese application No. 2019-545861; dated Sep. 29, 2021 (5 pages).

* cited by examiner

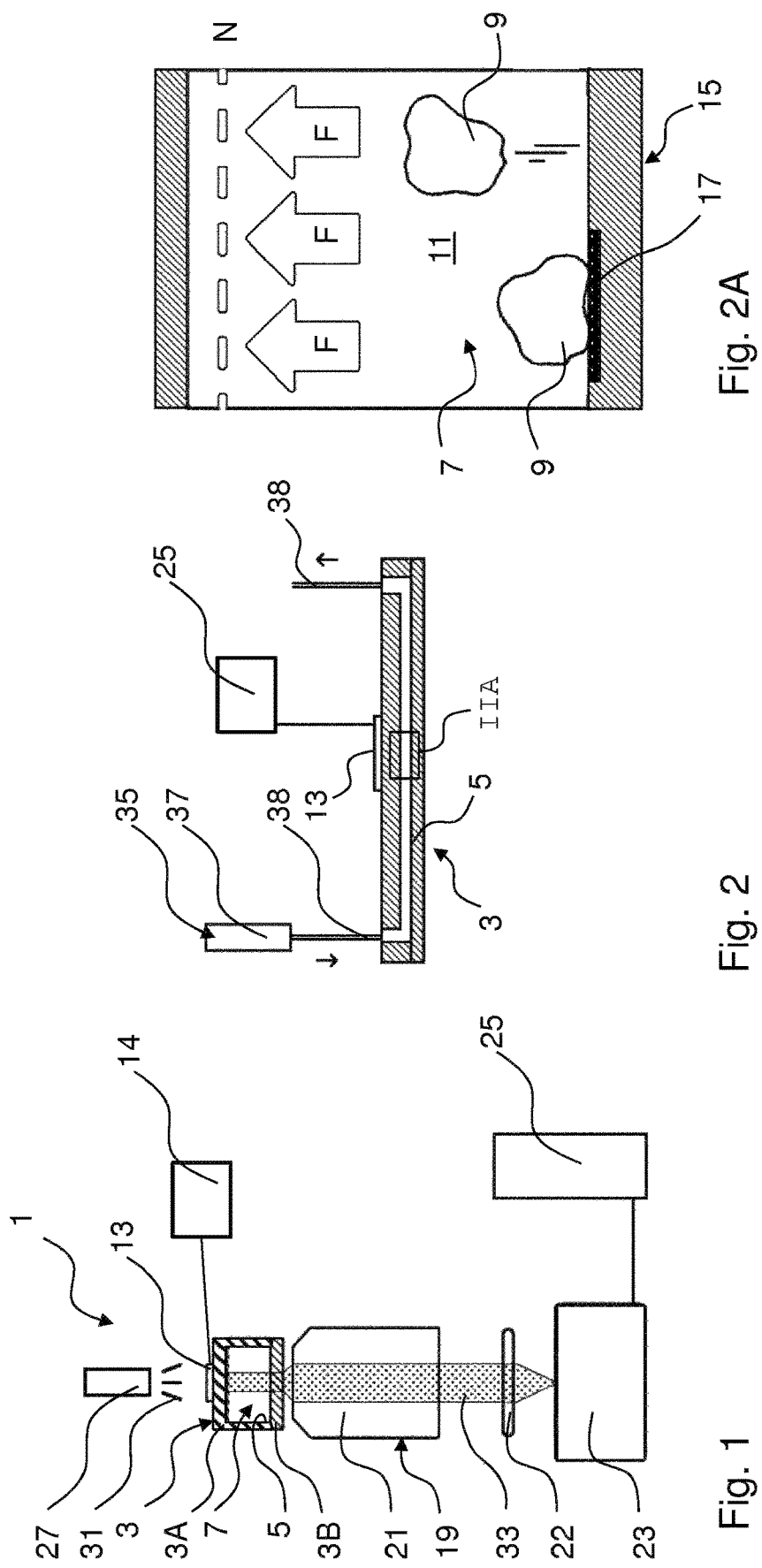

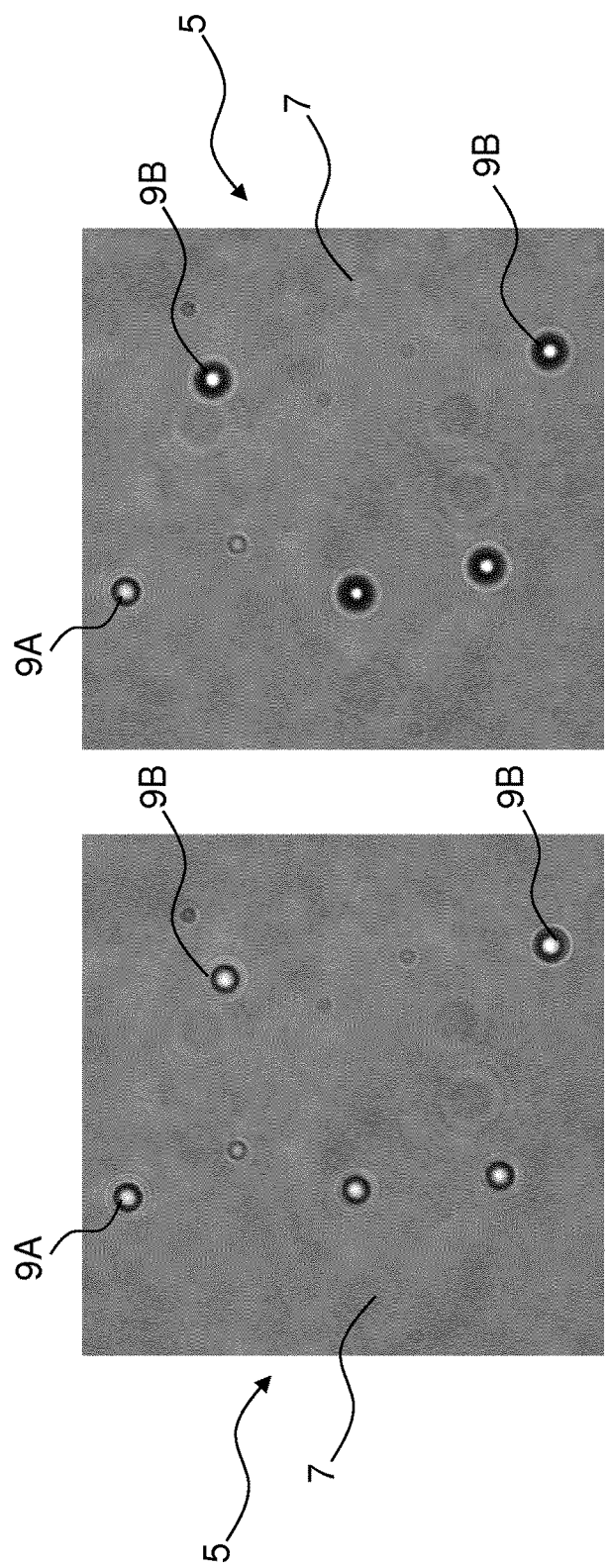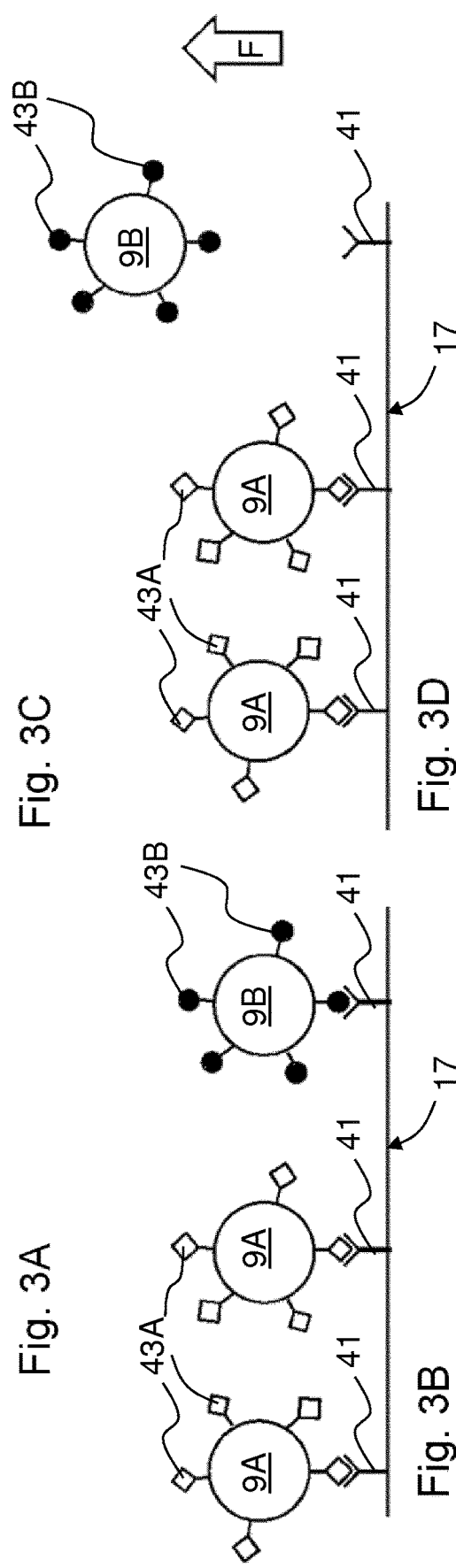
Fig. 3A  Fig. 3B  Fig. 3C  Fig. 3D

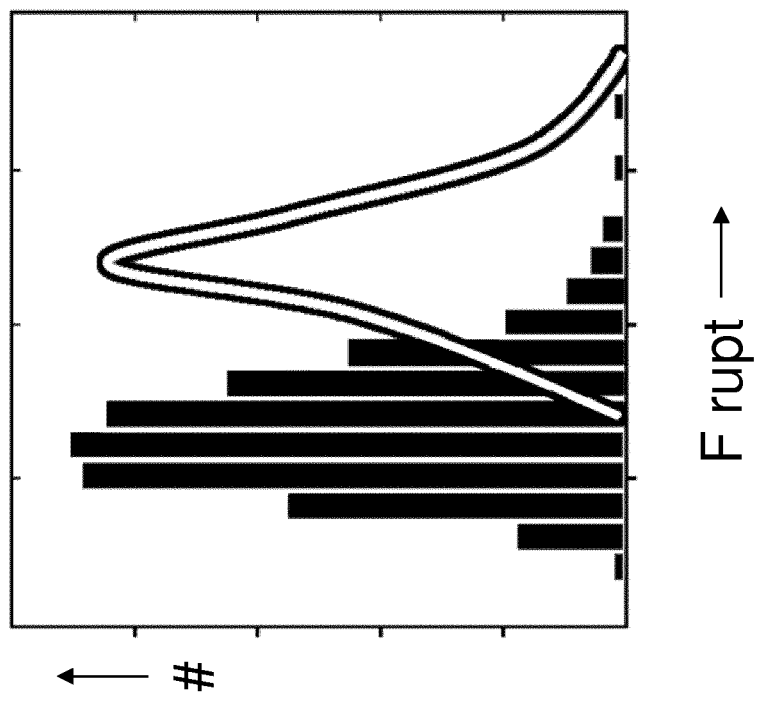
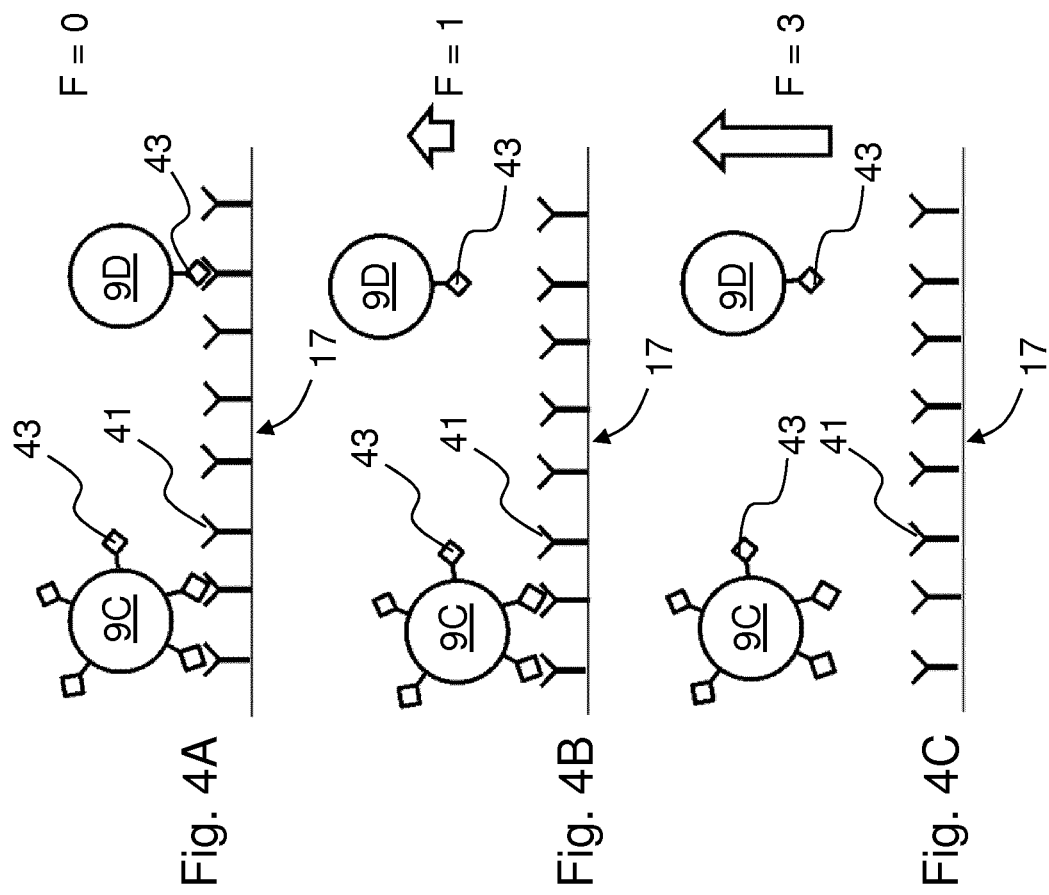
Fig. 4A  Fig. 4B  Fig. 4C  Fig. 4D

METHOD AND SYSTEM FOR STUDYING BIOLOGICAL CELLS

CROSS-REFERENCE TO RELATED APPLICATIONS

This application is a continuation of U.S. patent application Ser. No. 16/346,056, filed on Apr. 29, 2019, which, in turn is a 371 continuation of PCT/EP2017/078090 filed on Nov. 2, 2017, which, in turn, claims priority to Netherlands patent application no. 2017705, filed on Nov. 2, 2016, the disclosures of which are hereby incorporated by reference in their entirety herein.

TECHNICAL FIELD

The present disclosure relates to methods and systems for studying biological cells.

BACKGROUND

Biological cells have an outer membrane. This membrane is the interface between the cell and its environment. The membrane therefore builds the platform for a variety of processes that involve membrane embedded biomolecules making physical contact with binding partners in the extra-cellular space.

Therefore, a number of techniques have been developed for studying cellular and subcellular processes by interaction with the cellular membrane, and techniques have been devised to quantify the components of the cell surface to obtain information on the specific cell type (aggressive breast cancer or not for example). Most techniques required physical interaction with the cell, however recently a number of force-field techniques have been developed, which however tend to require adhesion of foreign objects to the cell and/or are damaging to the cell, e.g. see the overview paper of A. P. Liu, "Biophysical tools for cellular and subcellular actuation of cell signalling", Biophys. J. 111: 1112-1118 (2016).

However, more powerful tools are sought after, in particular tools that provide stronger signals and if possible tools that are less prone to damage the cell. In view of that, herewith, a method of and system for manipulating and/or investigating cellular bodies are provided, based on acoustic forces.

It is noted that the use of acoustic forces to manipulate micron-sized particles and cells is known in general. E.g. WO 2014/200341 provides an example of an acoustic wave system for use in studying biomolecules attached to microbeads, further cell manipulation via ultrasound microbeams or "acoustic tweezers" is discussed in J. Lee et al. "Targeted cell immobilization by ultrasound microbeam", Biotechnol. Bioeng. 108:1643 (2011); and in D. Baresch et al. "Observation of a Single-Beam Gradient Force Acoustical Trap for Elastic Particles: Acoustical tweezers", Phys. Rev. Lett. 116:024301 (2016). Further, a summary of current research in acoustofluidics can be found in V. Marx, "Biophysics: using sound to move cells", Nature Methods, 12(1):41 (2015). Reviews are also presented in H. Mulvana et al., "Ultrasound assisted particle and cell manipulation on-chip", Adv. Drug Del. Rev. 65(11-12):1600 (2013); A. Lenshof et al. "Acoustofluidics 5: Building microfluidic acoustic resonators", Lab on a Chip, 12:684 (2012); M. Evander, J. Nilsson. "Acoustofluidics 20: Applications in acoustic trapping", Lab on a Chip, 12:4667 (2012).

However, all of these techniques suffer from low signal-to-noise ratio, slow detection, small sample size and/or only localised and indirect interaction with the cellular membranes of probed cells. Further developments for biological studies and/or for measuring samples of plural specimens are therefore still desired.

SUMMARY

In view of the above herewith a method of manipulating and/or investigating cellular bodies is provided. Further, a manipulation system for investigating biological cellular bodies is provided. Various embodiments and aspects of both are discussed below.

In accordance with the discussion above herewith a method of manipulating and/or investigating cellular bodies is provided. The method comprises the steps of: providing a sample holder comprising a holding space for holding a fluid medium; providing a sample comprising one or more cellular bodies in a fluid medium in the holding space; generating an acoustic wave in the holding space exerting a force on the sample in the holding space. The method further comprises providing the holding space with a functionalised wall surface portion to be contacted by the sample and the sample is in contact with the functionalised wall surface portion during at least part of the step of application of the acoustic wave.

Thus, interaction of the one or more cellular bodies in the sample with the functionalised wall surface portion may be studied, e.g. a relation of adhesion of the cellular body to the functionalised wall surface portion and (the force of) the acoustic wave. The presently provided method allows studying bonding forces of cellular bodies to the functionalised wall portion; the entire contact surface of a cellular bodies with the wall portion may be probed at once. This relates to the amount of bonds and the bonding force per bond. Moreover, plural cellular bodies may be studied simultaneously which may provide statistic distribution information within one or a few measurements.

The cellular bodies may be cell portions like subcellular organelles, cell nuclei, and/or mitochondria. However, the cellular bodies may also be unicellular or pluricellular, such as small clumped cell groups, plant or animal biopts, dividing cells, budding yeast cells, colonial protists, etc. The cellular bodies may also be animal embryos in an early stage of development (e.g. the morula-stadium of a mammal, possibly a human embryo). In particular cases different types of cellular bodies may be studied together. E.g., cellular bodies from a mucosal swab, blood sample, or other probing techniques could be used.

The sample fluid is any fluid substance in which the cellular body can move under the influence of an acoustic force and within the time scale of an acoustic force study, the cellular bodies should be able to fall through the fluid to a wall portion of the sample holder, in particular fall to or from the functionalised wall portion dependent on the spatial orientation of the sample holder and the direction of the acoustic force. Note that an acoustic force study may generally last from sub-seconds time periods to several hours and possibly even days; motion of cellular bodies in a range of sub-seconds to seconds is preferred. The fluid should be capable of transmitting and sustaining ultrasound waves for prolonged periods. Suitable fluids are liquids and gels, e.g. water, watery fluids, bio-compatible solvents, oils, gels, aerogels, hydrogels and bodily fluids, although sufficient optical clarity to allow imaging may be desired in any embodiment using optical studying (see also below).

The acoustic wave preferably is a bulk acoustic wave, which prevents localised forces and enables exerting forces on an entire cell. The acoustic wave preferably is a standing acoustic wave, which provides a well-defined force profile in the sample holder across the sample.

The method enables studies on various properties of the one or more cellular bodies. Particular examples are presence, absence and/or quantification of abundance of biomolecules on the cellular bodies, surface adhesion forces and/or adhesion kinetics of the cellular bodies, to the functionalised surface portion, differences in any of the above under influence of biological processes active in the cellular bodies.

Current cell-adhesion assays and methods that aim for analysing cell-surface biomolecule composition and abundance, require a large quantity of cells, are very laborious and depend on expensive instrumentation, e.g. requiring labelling and risking damage to the cell(s) to be studied (e.g. cell-lysis, antibody labelling). Furthermore, these techniques typically lack the ability to assess cell-adhesion forces and cell-adhesion kinetics, in particular at the single cell level. The presently provided method enables studies on the various properties of multiple individual cellular bodies in parallel, since multiple cellular bodies in the sample may contact and interact with the functionalised wall surface portion. This may increase accuracy of the study results and false positives or false negatives may be avoided.

The presently provided method enables studies on cellular bodies per se, without adhesion of foreign objects to the cellular bodies such as microbeads, magnets, chromophores, antibodies, various other labels etc. which is generally required in present-day cell manipulation and -study techniques. The cellular bodies may remain essentially unharmed by the present method and it is envisioned that after performing the method, the cellular bodies could be administered to a test subject and/or returned to a subject having donated the cellular bodies for studying; e.g. one or more of T-cells, leukocytes, erythrocytes and similar cellular bodies may be withdrawn from a subject, be studied in accordance with the method, and could thereafter be further analysed with various other methods (single-cell sequencing, fluorescence microscopy, cryo-electron microscopy, etc.) and/or administered to another subject (e.g. blood donation) or returned to the original subject itself. Smaller cellular bodies, e.g. taken from blood plasma, may also be studied prior to donation or return. Similarly, spermatozoa and/or eggs could be studied before artificial in-utero or in-vitro fertilisation, and fertilized eggs and/or first-stage embryos (e.g. morula or blastula stage) may be screened before implantation in a female subject for gestation.

Suitable interaction moieties may comprise an antibody for selective binding to a particular target, e.g. a microbial cell or a cancer cell. E.g., specific antibodies exist for several major hospital infections. Such interaction moiety may normally be effective to deliver a conjugate of the interaction moiety to a predetermined pathological site in a mammal. A pathological site may comprise a target moiety which, together with the interaction moiety, constitutes a specific binding pair. In the present case the interaction moiety may be attached to the wall in the functionalised wall portion, e.g. by direct attachment or by forming the interaction moiety from or with a primer, and a binding pair may have sufficient binding force to adhere the cellular body to the functionalised wall portion.

The interaction moiety may comprise an antibody, or an antibody fragment that binds to a cell-surface antigen, or a ligand or ligand fragment that binds specifically to a cell surface receptor. From this group anti bodies, or antibody fragments, that bind to a cell-surface antigen may be preferred because of their binding selectivity. For instance, cancer cells usually have tumor associated antigens on their surface. Their complementary antibodies will bind very selectively to these tumor associated antigens. Ligand or ligand fragments however are also suitable. Various peptides are known to bind their cognate receptors with high affinity and thus would be suitable ligands for conjugation to the radioisotopes of the invention. Receptors are plasma membrane proteins which bind molecules, such as growth factors, hormones and neurotransmitters. Tumors develop from particular cell types which express certain subsets of these receptors. Taking advantage of this binding affinity between receptor and ligand enables target-specific studies and/or identification of cellular bodies.

Similarly, immune response relies on a complex interaction cascade between immune cells and their cell surfaces. For instance, B-cell activation depends on the binding of the B-cell receptor expressed on the B-cells surface to an antigen exposed on the surface of an antigen-presenting cell (APC). This in turn triggers a cascade of intracellular and intercellular events that leads to antibody secretion and pathogen attack by the complement system. Likewise, T-cell activation occurs via the interaction of an antigen on the surface of an APC with the T-cell receptor on the T-cell surface. Furthermore, T-cells recruitment to inflammatory/infected sites relies on the extravasation of T-cells from the bloodstream into tissue. Extravasation is initiated by a cytokine-regulated multistep adhesion process to the vascular epithelium followed by transmigration through the cell wall of blood vessels. Immunodeficiency and autoimmune diseases represent a misbalance in immune response. In all processes that can lead to abnormal immune response, e.g. altered lymphocyte activation, cell-adhesion, cell-migration and pathogen attack, the interaction of bio-molecules on the cell surface with binding partners in the extracellular environment is essential.

Representative examples of receptor-ligand pairs are set forth below:

| RECEPTOR | LIGAND |
| --- | --- |
| Epidermal growth factor receptor | epidermal growth factor (53 amino acids) |
| Platelet derived Growth factor receptor | platelet derived growth factor |
| Insulin like growth factor receptor | insulin-like growth factor |
| Glucagon growth factor receptor | glucagon (23 amino acids) |
| Vasopressin receptor | vasopressin (9 amino acids) |
| A thyroid stimulating Hormone receptor | thyroid stimulating hormone |
| Insulin receptor | insulin |

The method may comprise at least one of introducing sample fluid into the holding space and/or removing sample fluid from the holding space, e.g. flowing sample fluid through the holding space. This may in particular be done during at least part of the step of application of the acoustic wave, but before or after that is also possible. The introduced sample fluid may comprise one or more of the cellular bodies.

Thus, the sample may be introduced into the holding space and/or may be brought into contact with the functionalised wall surface portion during at least part of the step of application of the acoustic wave. Also or alternatively, sample parts that do not adhere to the functionalised wall surface portion may be displaced by the fluid flow so that a motion dynamic component, e.g. flow-induced lateral force component may be included in the study.

Such embodiment may also be used to do one or more of: priming the surface, introducing the sample, recovering the sample, exerting a force, transporting (part of) a sample within the sample volume, introduction of one or more modulators of the sample and/or a primer for the functionalised wall surface portion. Modulators may, e.g. comprise nourishing or noxious substances, or bioactive specimens to study their effects on cellular properties.

In an embodiment, the functionalised wall surface portion is provided with one or more primers. The primers may comprise one or more types of interaction moieties. In particular the functionalised wall surface portion is provided with one or more substances comprising at least one of antibodies, peptides, biological tissue factors, biological tissue portions, bacteria, antigens, proteins, ligands, cells, tissues, viruses, (synthetic) drug compounds, lipid (bi)layers, fibronectin, cellulose, nucleic acids, RNA, small molecules, allosteric modulators, (bacterial) biofilms, "organon-a-chip", etc., and/or specific atomic or molecular surface portions (e.g. a gold surface) to which at least part of the sample tends to adhere with preference relative to other surface portions, as also indicated elsewhere in this disclosure.

The method therewith provides for a wide variety of studies and/or interactions, which may e.g. be predominantly of a physical or a chemical or a biological nature, but any other nature in between or mixed may be apparent.

An embodiment comprises varying at least one of one of frequency and amplitude of the acoustic wave in the holding space, preferably time-dependent.

Thus the force exerted on the sample in the holding space may be adjusted. By varying the force time dependent, one or more of adhesion strength, adhesion dynamics and (adhesion) kinetics may be studied.

An embodiment further comprises the step of detecting and/or monitoring at least one property of at least one of the cellular bodies. The at least one property comprises, or is, at least one of: cell integrity, adhesion of a cellular body to at least part of the functionalised wall surface portion, motion of at least one of the cellular bodies, fluorescence emission, viability signs of at least one of the cellular bodies, interaction with an acoustic wave etc. The step of detecting and/or monitoring comprises optical detection, e.g. a light intensity detection and/or optical imaging by one or more of photographing, filming, microscopy. Also or alternatively, acoustic detection, e.g. surface acoustic detection, may be employed.

An optical signal may be dependent on an amount of cellular bodies adhered to the functionalised wall surface portion. Another optical signal may be dependent on a position of one or more cellular bodies in a 1-dimensional, 2-dimensional and/or 3-dimensional volume, possibly also time dependent.

In an embodiment, one or more cellular bodies may be studied using interference based tracking. E.g. a detector device is provided which comprises a detector to produce a (possibly digital) image of a focal plane of the detector and/or of a light source. The detector device may be or comprise a camera. Then, an interference pattern, in particular a diffraction pattern, may be caused by cells that are not in focus. By processing such interference pattern or a series of such interference patterns, a position and/or a position change of one or more cellular bodies in a perpendicular to the focal plane may be calculated. A series of such calculated positions may, possibly combined with time stamps, be used to track movements of such cellular bodies in the perpendicular direction. This may be combined with lateral positions of the cellular body to obtain higher dimensional tracking. The illumination may preferably comprise plane wave front illumination, e.g. provided by Light Emitting Diodes (LEDs).

The method may comprise at least one of: cell sorting; tracking motion of one or more cellular bodies as a function of at least one of acoustic force, flow of sample fluid and composition of sample fluid; monitoring an optical activity of one or more of the cellular bodies, e.g. luminescence (such as phosphorescence, fluorescence, bioluminescence, photosynthesis, spectral absorption differences, etc.); varying a temperature and/or a temperature profile of the sample holder; varying an illumination and/or illumination profile of the sample holder; varying a composition of the sample fluid. Such techniques enable various studies of (sub-)cellular processes affecting the membrane and/or bonding processes itself. E.g., cell sorting may be performed by bringing at least part of the sample in contact with the functionalised wall surface portion, generating a first acoustic wave in the holding space exerting a first force on the sample in the holding space, therewith causing separation from the functionalised surface portion of a first amount of cellular bodies of the sample, displacing the first amount of cellular bodies, and generating a second acoustic wave in the holding space exerting a second force on the sample in the holding space, different from the first acoustic wave and first force, respectively, therewith causing separation from the functionalised surface portion of a second amount of cellular bodies of the sample, and displacing the second amount of cellular bodies. By virtue of the different acoustic waves and forces, different types of cellular bodies are selectively displaced enabling identification and/or separation of the different types of cellular bodies. The displacement may comprise removal from the holding space and possible from the sample holder altogether. Optical effects may be affected by cellular interaction with interaction moieties on a surface. In an embodiment, the method comprises the step of quantifying an adhesion strength between at least one of the cellular bodies and a functionalized surface portion.

A force at which a cellular body is removed (the rupture force) from the functionalized surface can be determined by measuring the velocity at which the cellular body detaches from the surface portion. This velocity may be measured by tracking the cellular body in time. By assuming that the cellular body is spherical, the force on the cellular bodies can be estimated by Stoke's law: $F\_acoustic = F\_drag = 6\Pi\eta Rv$, with $\eta$ the dynamic viscosity of the medium (here: the sample fluid at the body's position), $R$ the cellular body's radius and $v$ the cellular body's velocity relative to the sample fluid in the direction of the force. This may also be used to calibrate an effective acoustic force versus an applied acoustic signal. One or more microbeads or other known particles may be included in a sample as reference objects for calibration.

In accordance with the presented method embodiments, an embodiment of the system comprises a sample holder comprising a holding space for holding a sample comprising one or more biological cellular bodies in a fluid medium, and an acoustic wave generator connectable or connected with the sample holder to generate an acoustic wave in the holding space exerting a force on the sample. Typically, for the fluid, water or a water based buffer is used. However also oils and (hydro)gels could be used. In case of a sample comprising patient material, the fluid could be a bodily fluid. The sample holder comprises a wall providing the holding space with a functionalised wall surface portion to be contacted, in use, by at least part of the sample.

The system, in particular the sample holder, may be designed in such a way that an acoustic amplitude maximum is located at or near the functionalised wall surface, or that (high) forces to which the cellular bodies are (expected to be) particularly susceptible are predominantly sensible at or near this functionalised wall surface.

The sample holder may comprise a recess forming the holding space. The sample holder may be unitary or constructed from plural objects, e.g. a part that is at least locally U-shaped in cross section and a cover part to cover and close the U-shaped part providing an enclosed holding space in cross section. The enclosed holding space may be enclosed in all directions, or it may have one or more entrance and/or exit ports, e.g. forming a continuous channel.

The acoustic wave generator may be permanently attached to the sample holder, possibly integrated in a portion of the sample holder. In another embodiment the acoustic wave generator may be repeatedly attachable to the sample holder, or be connected to form an acoustic cavity with the sample holder via an acoustic transmitting medium. As examples, ultrasound waves may be generated by piezoelectric generators, electromechanical generators, optical generators (e.g. subjecting a portion to a series of laser pulses), and other techniques, possibly in combination. For creation of a standing wave the sample holder including the sample fluid and possibly structures attached to the sample holder may form an ultrasound cavity for particular frequencies, in one or more directions. The sample holder may then be designed to prevent or to promote mode-mixing of different and/or differently oriented acoustic modes.

The acoustic wave generator may comprise or be a bulk acoustic wave generator to generate a bulk acoustic wave in the holding space and/or in a sample contained therein.

In an embodiment, the functionalised wall surface portion is provided with one or more primers. The primers may comprise one or more types of interaction moieties and/or precursors thereof. In particular the functionalised wall surface portion is provided comprising at least one of antibodies, peptides, biological tissue factors, biological tissue portions, bacteria, antigens, proteins, ligands, cells, tissues, viruses, (synthetic) drug compounds, lipid (bi)layers, fibronectin, cellulose, nucleic acids, RNA, small molecules, allosteric modulators, (bacterial) biofilms, "organ-on-a-chip", specific atomic or molecular surface portions (e.g. a gold surface) to which at least part of the sample tends to adhere with preference relative to other surface portions, nanostructured or microstructured surface portions e.g. micropillars, microridges, etc.

By providing the functionalised surface portion with one or more primers, particular predetermined interactions between the cell(s) of the cellular body and the functionalised surface portion may be influenced or caused on contact of the cellular body with such portion. E.g. a cellular body may adhere to the wall. Also, one or more other biological processes in or on the cell(s) of the cellular body may be influenced or caused, which may be studied in the system.

In an embodiment the functionalised wall surface portion comprises plural mutually differently functionalised wall surface portion portions to be contacted by the sample.

This facilitates studying different predetermined interactions between the cellular body and the functionalised surface portions.

The different portions may be formed using various techniques, e.g. printing, and may be arranged in various patterns, possibly with repetitive portions.

In an embodiment, the sample holder is connected or connectable to a flow system for introducing a fluid into the holding space and/or removing a fluid from the holding space, e.g. for flowing fluid through the holding space. The fluid flow system may be comprised in the manipulation system. The fluid flow system may comprise one or more of reservoirs, pumps, valves, and conduits for introducing and/or removing one or more fluids, sequentially and/or simultaneously.

Fluid that thus is introduced into, removed from or flowed through the holding space may comprise sample material, e.g. one or more of sample fluids, cellular bodies, actors on the cellular bodies, etc. Thus, one or more parts of a sample may be recovered after an experiment and/or different sample conditions may be provided, e.g. one or more of different pH-values, different dilutions such as salt concentrations, different fluid compositions, and different cellular bodies sequentially or in parallel. Also, actors on cellular bodies may be introduced, e.g. nutrients, chemical substances, viruses, etc. The fluid may also comprise one or more dissolved or, in particular in hydrogel and/or aerogel-based fluids, entrained gases, like $N_2$, $CO_2$, $O_2$, noble gases, like Ne, Ar, noxious gases like CO, $O_3$, $NO_x$, and other gases that may have a biological effect such as cyanide-containing gases, ethylene, etc. The gas may also be a gas mixture of different components, with a controlled composition or with an uncontrolled composition like ambient air. It is considered that acoustic index variations which may disturb a desired acoustic force profile within the holding space, such as density variations in the fluid, in particular gas bubbles of a size in the order of an interior dimension of the holding space such as spanning a significant portion of a width and/or height of the holding space, should be prevented, at least during study of the sample. However, microbubbles with a size on the order of about tenth of an interior dimension of the holding space or less, e.g. smaller than about 5 micrometers for a holding space of about 50 micrometers height and/or width, respectively, could be used as one or more of image reference, force concentrator, contrast object, force probe, etc. Note further that large bubble may be used to propel sample fluid through the sample holder and in such case may be used to benefit.

Control over the amount and/or composition of the fluid within the sample holder may also be used to control a sample volume.

The system may be configured to introduce the fluid into the holding space and/or remove the fluid from the holding space, e.g. flowing the fluid through the holding space, simultaneously with operation of the acoustic wave generator to generate an acoustic wave in the holding space exerting a force on the sample. Thus, a motion dynamic component, e.g. flow-induced lateral force component may be included in the study. The system may thus also be included in a flow cytometry system or other flow system, e.g. integration with an on-line flushing system.

The flow direction may be perpendicular to the direction of the acoustic force, or at least a main force direction component from that.

In an embodiment, the acoustic wave generator is controllable to adjust at least one of frequency and amplitude for generating adjustable acoustic waves, preferably time-dependent, wherein in particular the acoustic wave may be a standing wave.

This enables parameterised studies. In a particular case, the amplitude may be adjusted over at least two orders of magnitude. Acoustic frequencies may depend on the geometry of the sample holder but they generally may lie between 1 and 100 MHz. A sample holding space open size in any one of three perpendicular directions, e.g. height, width, length of the holding space may be in a range between 1 and 1000 micrometers, so that the holding space may typically have a volume in a range of 0.1 microliter-100 microliters, or even up to a milliliter, with a large variety of geometries, like "lab on a chip" sample holders. Important is that the sample holder can provide and sustain the acoustic wave effectively in the sample.

A single cellular body or a plurality of cellular bodies may be manipulated and/or measured simultaneously. A large plurality of cellular bodies may form a surface bulk, e.g. a bacterial colony. In an embodiment, plural individual cellular bodies may be manipulated and/or measured separately but in parallel, as opposite to surface bulk studies.

The acoustic wave signal may vary over several orders of magnitude, e.g. lasting from sub-second to tens of minutes or even longer, depending on the nature and robustness of the sample and processes in it.

A suitable frequency of the acoustic wave may be determined by the dimensions of at least a portion of the sample holder (either or not in combination with the acoustic generator), e.g. the acoustic cavity; the frequency may be a resonance frequency of the acoustic wave in that portion, possibly being associated with a standing acoustic wave in that portion. An optimum frequency may be determined beforehand and/or in operation. It is considered that a resonance frequency may exert an acoustic force of several orders of magnitude higher than a non-resonant acoustic wave.

A time dependent adjustment may enable studies based on predetermined frequency and/or amplitude patterns, e.g. pulses, ramps, repetitive modulations and/or sweeps such as frequency chirps. Different frequency spectra may be applied as well. Using such techniques particles may be manipulated selectively or collectively, e.g. by pushing or pulling.

The system may comprise plural acoustic wave generators, which may be arranged for generating acoustic waves which mutually differ with respect to at least one of frequency, amplitude, and a time dependency of the respective frequency and/or amplitude and/or of which at least one is controllable to adjust a frequency and/or an amplitude of the respective acoustic wave for generating adjustable acoustic waves, preferably time-dependent. One or more further acoustic wave generators may thus be provided for generation of complex force fields, in a particular embodiment acoustic wave generators are connected with the sample holder to generate acoustic waves in the holding space from perpendicular directions, which may be separately controllable.

According to an embodiment the manipulation system comprises a detector for detecting a response of the one or more cellular bodies to (a force exerted by) the acoustic wave. Effects of the manipulation of the one or more cellular bodies may therewith be investigated.

The detector may comprise an optical detector. The optical detector may comprise a photodiode, an array of photodiodes, a camera and/or a microscope, but for particular experiments a photocell without image resolution could also suffice, e.g. for bulk measurements. Digital photo and/or film cameras are considered suitable, preferably having an adjustable imaging frame rate. The detector may be wavelength selective, e.g. comprising one or more colour filters. Possibly plural detectors are provided which are wavelength selective for different wavelengths.

In a particular embodiment, the detector comprises a confocal microscope and/or superresolution microscope, e.g. a (near field) scanning optical microscope ("SOM"/ "NSOM"), structured illumination microscope ("SIM"), multicolour excitation light sources.

Typically, bright field illumination may be used, e.g. LED-illuminated. However, dark field imaging may also be employed. Using software (portions of) the sample may be studied with an accuracy below the diffraction limit, even if the microscope itself is not a superresolution microscope. The detector does however not have to be a microscope. If one would only measure the presence of cells at the surface a simple detector, e.g. with total internal reflection fluorescence microscopy ("TIRF microscopy") would suffice. Other options include surface plasmon resonance detection and/or lensless imaging (e.g. imaging without lenses by placing a camera chip directly under the sample).

Further, acoustic detection may be employed; Surface acoustic waves enable detection of objects on the surface, e.g. by effects on the wave, like differences in amplitude, phase and/or direction of propagation due to absorption and/or reflection of acoustic energy etc. Thus, it is possible to acoustically manipulate cellular bodies with a bulk acoustic wave and detect with a surface acoustic wave along the respective surface the amount of cellular bodies residing on, in particular being bound to, the surface. A suitable acoustic detector comprises a piezo actuator serving as sensor element.

Although contact detection and/or other forms of detection may be used in combination with acoustic force studies, optical detection may be preferred since this may be done with little to no effect on or interaction with a biological cellular body. Further, many different proven optical techniques and systems are available. For optical detection, the system may be provided with a light source. The light source may be polychromatic or monochromatic, which may cause or rather preclude optical interaction with (portions of) the sample and which may reduce or prevent optical (chromatic) aberrations for optical detection. Optical detection relying on any of optical interference, refraction, diffraction, may benefit from a light source providing illumination with plane wave fronts or otherwise controlled wave fronts at the location of the sample.

In embodiments, the system comprises one or more of a light source, a memory, a tracking system for tracking one or more of the cellular bodies and a controller for performing microscopy calculations and/or analysis associated with the microscopy detection technique. The tracking system may be configured to perform 2-dimensional ("2D") and/or 3-dimensional ("3D") tracking. In an embodiment, 3D tracking can be used to determine a speed of a cellular body through a surrounding medium, which may also be used to determine an acoustic force of the system on the cellular body and/or interaction of the cellular body with an acoustic force of the system. The tracking system and/or the controller may also be connected with the acoustic wave generator to control operation of the system.

The system may comprise a sensor and a controller connected or connectable with the acoustic wave generator for controlling operation of the acoustic wave generator in response to a signal from the sensor. Thus, a feedback system may be provided.

Nevertheless, the system and method may already be highly effective and beneficial in just quantifying, in absolute numbers and/or as relative fractions, an amount of cellular bodies adhering to the functionalised surface, without detailed study into an interaction or single-body behaviour.

In an embodiment, the system comprises for manipulating one or more of the cellular bodies one or more of an optical tweezers system, a magnetic tweezers system, an electrostatic tweezers system and contact probes, wherein one or more of the cellular bodies may be accordingly prepared and a preparation system for that may be provided.

In an embodiment, the system comprises a light source for excitation and/or interrogation of one or more optically active portions in the sample, e.g. chromophores, etc., e.g. for using fluorescence detection. The light source may comprise a laser, the light source preferably is wavelength tuneable.

The system may be provided as a stand-alone system, as a worktop-instrument or even as a hand-held instrument.

An embodiment further comprises a detector to produce a digital image of a focal plane and wherein the system is provided with a calculation device to calculate a position of one or more of the cellular bodies in a direction perpendicular to the focal plane by processing of an interference pattern caused by one or more of the cellular bodies which are not in focus. This enables interference detection and determining and tracking cellular bodies in a direction along an imaging direction, perpendicular to a direction of the acoustic wave and/or the functionalised surface. An embodiment may comprise a thermal element for adjusting a temperature and/or a temperature profile of the sample holder. The thermal element may comprise a simple electrical heater wire or a more intricate element like one or more Peltier elements which may enable precise thermal control and which may provide both heating and cooling.

In a further aspect a sample holder for the system and/or method described herein are provided. The sample holder comprises a holding space for holding a sample comprising one or more cellular bodies in a fluid medium, and an acoustic wave generator connected with the sample holder to generate an acoustic wave in the holding space exerting a force on the sample, wherein the sample holder comprises a wall providing the holding space with a functionalised wall surface portion to be contacted, in use, by at least part of the sample.

The sample holder may be formed with a connecting portion to be connected with a corresponding counter connector of a device comprising associated ultrasound power generator and detection system, e.g. one or more of light sources and optical detectors, for provision of the system and/or performance of the method.

Thus a method and a system are provided that enable to detect the presence and/or quantify the abundance of biomolecules on a surface of a cellular body. The method and system allow to quantify adhesion kinetics and adhesion strength down to the single body level, as each individual cellular body may be different and interact differently with the functionalised surface, and up to hundreds or thousands of cellular bodies in parallel. The method and system each combine aspects of acoustic force spectroscopy, microfluidics, surface functionalization and live (super-resolution) video tracking of plural cellular bodies, possibly even single-cell live super-resolution video tracking, to perform force-spectroscopy on cellular bodies down to the single body level in a highly parallelized fashion. Generating resonant bulk acoustic waves within a microfluidic cavity allows to directly and instantly apply forces on the cellular bodies.

Note that, in a typical design, a microfluidic chamber forming the holding space itself does not form an acoustic cavity, rather a standing wave is formed across the whole sample holder (e.g. a chip including a piezo element, a top glass, a fluid layer and a bottom glass layer). If a standing wave is generated over a microfluidic layer only, the forces at the boundary may become very small and possibly be insufficient to detach any cellular bodies from the surface, which may impair detection possibilities. In combination with live (single-cell) video tracking the present techniques enables to precisely detect adhesion events of the cellular body and to quantify the adhesion forces that are conveyed by interactions of (bio)molecules on the surface of a cellular body and the functionalized wall surface portion of the microfluidic sample volume. Note that motion-detection may not require accurate position detection at any given time, and position determination of a sample portion at a particular time need not require detection and/or tracking of movement of the sample portion at that time.

BRIEF DESCRIPTION OF THE DRAWINGS

The above-described aspects will hereafter be more explained with further details and benefits with reference to the drawings showing a number of embodiments by way of example.

FIG. 1 is a schematic drawing of an embodiment of a manipulation system;

FIG. 2 is a schematic drawing of a sample holder for the system of FIG. 1;

FIG. 2A is a schematic detail of FIG. 2 as indicated;

FIGS. 3A-3D indicate interaction of cellular bodies in a sample with a functionalised wall surface portion of a sample holder, wherein the sample holder and the cellular bodies in it are subject (FIGS. 3C-3D) or not (FIGS. 3A-3B) to an acoustic wave on the sample holder exerting a force on the sample;

FIGS. 4A-4D indicate effects of varying a force on cellular bodies by acoustic waves in the holding space;

DETAILED DESCRIPTION OF EMBODIMENTS

Figure 5:
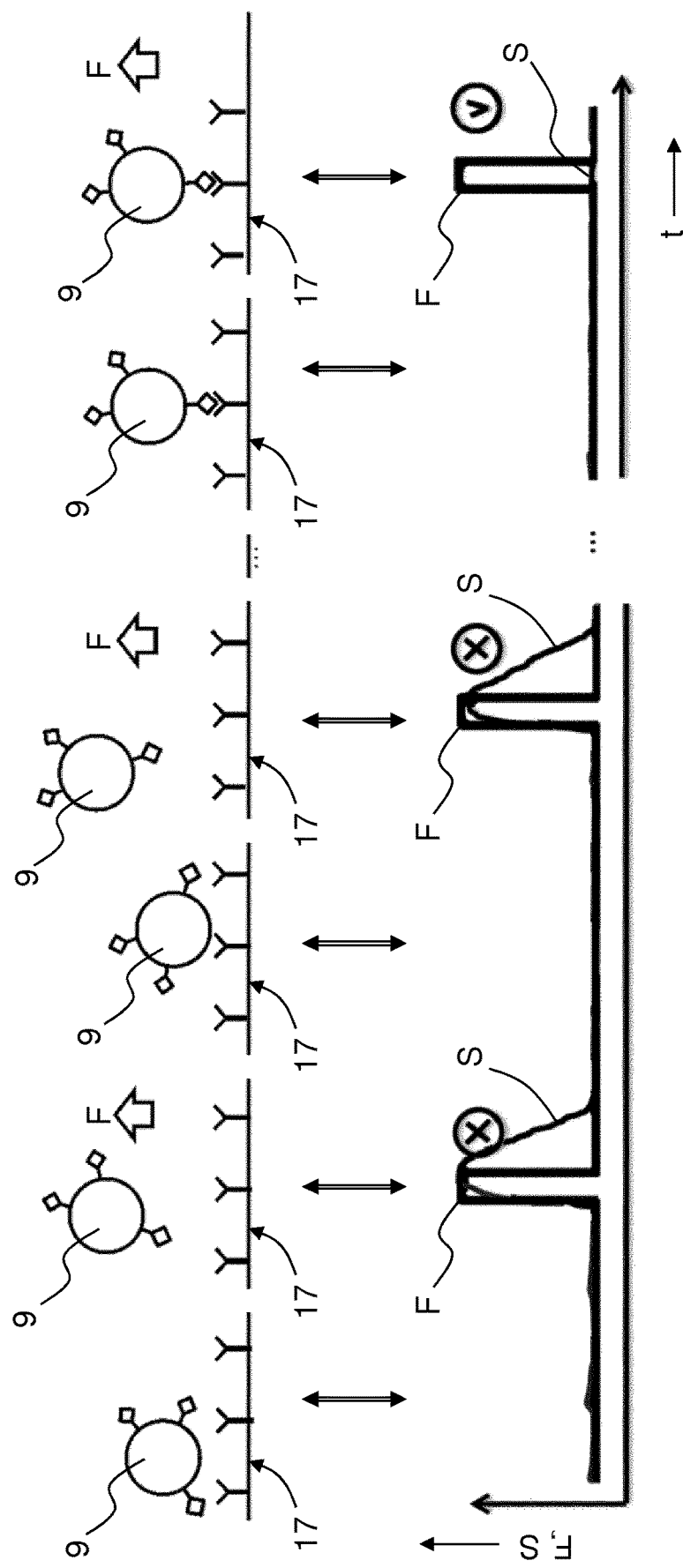
FIG. 5 indicates a method of studying interaction kinetics on cellular bodies by acoustic waves in the holding space.

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral, where helpful individualised with alphabetic suffixes.

FIG. 1 is a schematic drawing of an embodiment of a manipulation system 1 in accordance with the present concepts, FIG. 2 is a cross section of a sample holder and FIG. 2A is a detail of the sample holder of FIG. 2 as indicated with "IIA".

The system 1 comprises a sample holder 3 comprising a holding space 5 for holding a sample 7 comprising one or more biological cellular bodies 9 in a fluid medium 11. The fluid preferably is a liquid or a gel. The system 1 further comprises an acoustic wave generator 13, e.g. a piezo element, connected with the sample holder 3 to generate an acoustic wave in the holding space 5 exerting a force on the sample 7 and cellular bodies 9 in the sample 7. The acoustic wave generator 13 is connected with an optional controller 14 and power supply, here being integrated.

The sample holder 3 comprises a wall 15 providing the holding space 5 with a functionalised wall surface portion 17 to be contacted, in use, by part of the sample 7.

The shown manipulation system 1 comprises a microscope 19 with an adjustable objective 21 and a camera 23 connected with a computer 25 comprising a controller and a memory. The computer 25 may also be programmed for tracking one or more of the cellular bodies based on signals from the camera 23 and/or for performing microscopy calculations and/or for performing analysis associated with superresolution microscopy and/or video tracking, which may be sub-pixel video tracking. The computer or another controller (not shown) may be connected with other parts of the system 1 (not shown) for controlling at least part of the microscope 19 and/or another detector (not shown). In particular, the computer 25 may be connected with one or more of the acoustic wave generator 13, the power supply thereof and the controller 14 thereof, as shown in FIG. 1.

The system further comprises a light source 27. The light source 27 may illuminate the sample 7 using any suitable optics (not shown) to provide a desired illumination intensity and intensity pattern, e.g. plane wave illumination, Kohler illumination, etc., known per se. Here, in the system light 31 emitted from the light source 27 is directed through the acoustic wave generator 13 to (the sample 7 in) the sample holder 3 and sample light 33 from the sample 7 is transmitted through the objective 21 and through an optional ocular 22 and/or further optics (not shown) to the camera 23. The objective 21 and the camera 23 may be integrated. In an embodiment, two or more optical detection tools, e.g. with different magnifications, may be used simultaneously for detection of sample light 33, e.g. using a beam splitter.

In another embodiment, not shown but discussed in detail in WO 2014/200341, the system comprises a partially reflective reflector and light emitted from the light source is directed via the reflector through the objective and through the sample, and light from the sample is reflected back into the objective, passing through the partially reflective reflector and directed into a camera via optional intervening optics. Further embodiments may be apparent to the reader.

The sample light 33 may comprise light 31 affected by the sample (e.g. scattered and/or absorbed) and/or light emitted by one or more portions of the sample 7 itself e.g. by chromophores attached to the cellular bodies 9.

Some optical elements in the system 1 may be at least one of partly reflective, dichroic (having a wavelength specific reflectivity, e.g. having a high reflectivity for one wavelength and high transmissivity for another wavelength), polarisation selective and otherwise suitable for the shown setup. Further optical elements e.g. lenses, prisms, polarizers, diaphragms, reflectors etc. may be provided, e.g. to configure the system 1 for specific types of microscopy.

The sample holder 3 may be formed by a single piece of material with a channel inside, e.g. glass, injection moulded polymer, etc. (not shown) or by fixing different layers of suitable materials together more or less permanently, e.g. by welding, glass bond, gluing, taping, clamping, etc., such that a holding space 5 is formed in which the fluid sample 7 is contained, at least during the duration of an experiment. As shown in FIGS. 1 and 2, the sample holder 3 may comprise a part 3A that has a recess being, at least locally, U-shaped in cross section and a cover part 3B to cover and close (the recess in) the U-shaped part providing an enclosed holding space 5 in cross section.

As shown in FIG. 2, the sample holder 3 is connected to an optional fluid flow system 35 for introducing fluid into the holding space 5 of the sample holder 3 and/or removing fluid from the holding space 5, e.g. for flowing fluid through the holding space (see arrows in FIG. 2). The fluid flow system 35 may be comprised in a manipulation and/or control system. The fluid flow system 35 may comprise one or more of reservoirs 37, pumps, valves, and conduits 39 for introducing and/or removing one or more fluids, sequentially and/or simultaneously. The sample holder 3 and the fluid flow system 35 may comprise connectors, which may be arranged on any suitable location on the sample holder 3, for coupling/decoupling without damaging at least one of the parts 3, 35, and preferable for repeated coupling/decoupling such that one or both parts 3, 35 may be reusable thereafter.

FIG. 2A is a schematic of two cellular bodies 9 in the sample holder 3 of FIG. 2. Part of the wall 15 of the sample holder 3 is provided with a functionalised wall portion 17 (left side in FIG. 2A) and part is not (right side in FIG. 2A).

FIGS. 3A and 3C are microscopy images of an experimental situation in a viewing direction perpendicular to a functionalised wall portion of a sample holder (not discernible in FIG. 3A, 3C). Five cellular bodies 9A, 9B in a sample fluid 7 in the sample holder are visible.

FIGS. 3B and 3D are schematic depictions of the situations of, respectively, FIGS. 3A and 3C, in a viewing direction along the functionalised wall portion 17 of a sample holder (i.e. perpendicular to FIGS. 3A, 3C, respectively, comparable to FIG. 2A).

In each case, the functionalised wall surface portion 17 is provided with one or more primers. The primers may comprise one or more types of interaction moieties.

FIGS. 3B, 3D each indicate the functionalised wall surface portion 17 of a wall 15 of a holding space 5 of a sample holder 3 of an embodiment of system 1 in sideways cross section view. The wall surface portion 17 is functionalised with interaction moieties 41, e.g. antibodies, which in this example are of a single type. Cellular bodies 9A, 9B comprising different target moieties 43A, 43B, e.g. antigens 43A, 43B, of a sample are brought into contact with the functionalised wall surface portion 17 and the cellular bodies 9A, 9B (are let to) engage with the interaction moieties 41.

FIGS. 3A-3B show a situation at rest wherein no acoustic wave is applied to the holding space. FIGS. 3C-3D show a situation wherein an acoustic wave is applied to the holding space, exerting a force F to the cellular bodies 9A, 9B in the sample (see arrows in FIG. 2A and FIG. 3D). The acoustic wave is a bulk acoustic wave having a direction of propagation perpendicular to the wall 15. The acoustic wave may be a travelling wave or, preferably, a standing wave. Thus, the force F is in a direction of propagation perpendicular to the wall 5 (see arrow) towards a node in the acoustic field indicated with dashed line N in FIG. 2A. Note that the position of a node in the sample holder, which may be a nodal line or nodal plane, and/or the strength of the acoustic force may be adjusted by proper selection of one or more of the acoustic frequency, the acoustic power, the sample holder geometry, and the composition (e.g. viscosity) of the fluid medium.

In the sample of FIG. 2A, cellular bodies 9 adhered to the functionalised wall surface portion 17 remain attached (left side) and cellular bodies 9 aside from the functionalised wall surface portion 17 are lifted from the wall 15 (right side).

In the sample of FIGS. 3A-3B, some interaction and target moieties 41 and 43A match and form a strongly bound binding pair, binding the respective cellular bodies 9A strongly to (the functionalised wall portion 17 of) the wall 15. Other interaction and target moieties 41 and 43B do not match and form a loosely bound binding pair or do not bind at all, so that the respective cellular bodies 9B are released from (the functionalised wall portion 17 of) the wall 15 under influence of the force F. In the microscopy images of FIGS. 3A, 3C this is visible by the respective cellular bodies 9A, 9B being in focus or moving out of focus of the microscope.

Hence, by observing a response of the cellular bodies to the application of a force by an acoustic wave to the sample, binding interactions may become detectable. E.g., this enables distinguishing (properties of) different cellular bodies 9A, 9B. In an embodiment wherein a fluid flow is applied to the sample parallel to the wall 15, detached cellular bodies 9B may be moved, e.g. washed away, whereas cellular bodies 9A remaining adhered to the wall 15 may stay in place. This enables separation of cellular bodies 9A, 9B.

Note that instead of having (had) no particular coating or treatment as in FIG. 2A, a wall portion adjacent to a non-functionalised wall surface portion may be provided with e.g. or a non-stick coating such as polytetrafluoroethylene (PTFE, "Teflon"®), or with a differently functionalised wall surface portion e.g. comprising antibodies matching the antigens of cellular bodies detached from an upstream functionalised wall surface portion and binding the latter to the adjacent functionalised wall surface portion.

FIG. 4A-4C show two cellular bodies 9C, 9D of a sample 5, having the same target moieties 43 but in different amounts. The cellular bodies 9C, 9D interact with (interaction moieties 41 on) a functionalised wall surface portion 17 and they are subjected to a force F of acoustic waves on (the cellular bodies in) the sample by variation of the amplitude of the acoustic waves. In FIG. 4A the force F is 0 (cf. FIG. 3B) and both cellular bodies 9C, 9D are adhered to the wall surface portion 17. In FIG. 4B the force F is 1 unit which is sufficient to break the binding of the interacting moieties 41, 43 of one cellular body 9D to the wall surface portion 17 and to detach the cellular body 9D. In FIG. 4C the force is increased to 3 units which is sufficient to break also the binding of the interacting moieties 41, 43 of the other cellular body 9C to the wall surface portion 17 and detach also the cellular body 9C. Suitable binding forces of single cells to a surface are in the order of picoNewtons (pN), and forces applicable with acoustic waves, in particular standing bulk acoustic waves, have been achieved on microbeads in a range from about 0.1 pN up to a few thousands of pN.

Consequently, by observing a response of the cellular bodies 9C, 9D to a variation in the force of the acoustic wave to the sample, strengths of binding interactions may become detectable which enable quantification of target moieties on cellular bodies.

FIG. 4D indicates a statistical analysis of measured binding forces, i.e. the force required to rupture the binding F_rupt, of plural normal healthy cells to a wall surface portion functionalised with antibodies as the interaction moieties (histogram). In some cases, disease afflicted cells may form more antigens (target moieties) on their membrane than healthy cells, causing a stronger binding force to (the antibodies of) the functionalised wall surface portion; compare FIGS. 4A-4C. This is detectable in the adhesion statistics (curve, based on simulation). Similarly, a reduction in target moieties, e.g. due to underexpression of a gene, may be detected by reduced binding strength of afflicted cells comparable to healthy cells.

Also, or in addition to varying the amplitude of the acoustic wave, the frequency of the acoustic wave may be varied, to affect and study interaction moiety—target moiety binding parameters. Results may be obtained in a similar way as indicated in FIGS. 4A-4D.

FIG. 5 indicates schematically in similar fashion to FIGS. 3A-4D, and in a graph versus time t, how adhesion dynamics may be studied by varying the force F applied to the sample 5 in a sequence of off-on pulses (different panels in the schematic depiction as indicated with arrows) and measuring a signal S indicative of a variation of one or more properties of a cellular body 9 under consideration, e.g. visibility, mobility, etc. This may provide further information about the studied cellular body. E.g., it may indicate a likelihood that a cell adheres to a particular antibody (marked "v") or not (marked "x"). The acoustic force may also be varied differently, e.g. gradually. E.g. in an experiment, a difference may be studied between abruptly stopping the acoustic force and dropping the cellular body onto the surface versus a gradual decrease of the acoustic force therewith slowly bringing the cellular body closer to the functionalised surface.

Figure 6A:
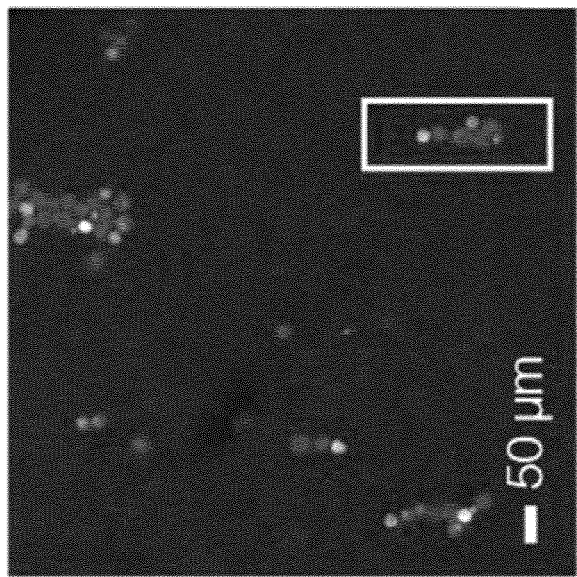
FIGS. 6A-6C show experimental results.
Figure 6B:
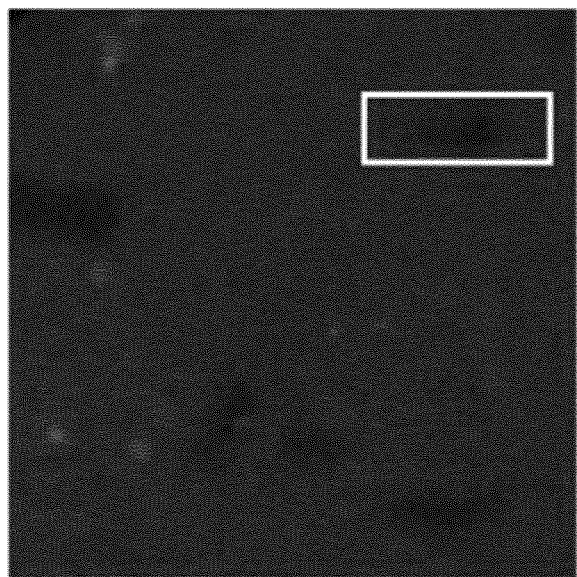
Figure 6C:
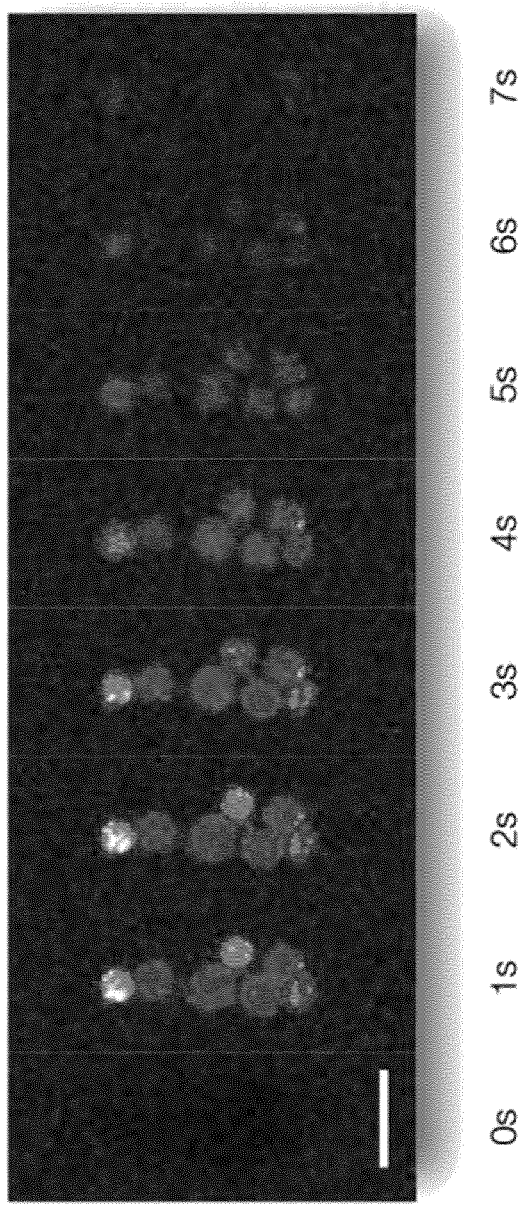

FIGS. 6A-6C show experimental results with biological cells imaged with confocal fluorescence. FIGS. 6A and 6B are images of one portion of a sample at different times, FIG. 6C shows a series of images from the detail indicated in FIGS. 6A, 6B at different times, as discussed hereafter. In this example, the focal plane of the microscope was positioned to coincide with an acoustic node, i.e. the location to which the cells are urged. At the start of the experiment, t=0 seconds (FIG. 6A; FIG. 6C at t=0 s), no acoustic signal is applied and all cells in the sample are sedimented to the bottom of the holding space and no cells are visible. Thereafter, the acoustic force is switched on, cells are forced from the surface to the acoustic node and a number of (clumps of) cells become visible at t=1 second, see FIG. 6B and FIG. 6C at t=1 s. During application of the acoustic force, the cells remain trapped at the acoustic node and remain visible (FIG. 6C at t=2 s). After 2 seconds of applied acoustic force the force is turned off and the cells slowly sediment again, dropping from view within a few seconds (FIG. 6C at t=3 s . . . 7 s). The different brightness (and different colours in the original images) of different cells in FIGS. 6B, 6C suggest that different types of cells were present in the sample but that was not studied in this experiment.

It will be clear to the reader that other imaging methods can be used concurrent with acoustic manipulation of cellular bodies.

Figure 7A:
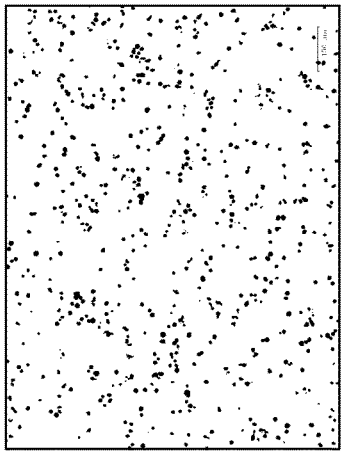
FIGS. 7A-9C show further experimental results.
Figure 8A:
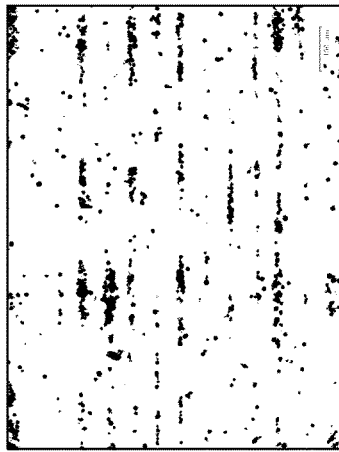

FIGS. 7A-9C indicate use of the presently presented techniques in sorting T-cells based on avidity (the strength with which they bind to binding partners). Experiments were conducted as follows: a melanoma patient-derived tumour cell line was cultured inside a sample holder such that the culture adhered to a wall portion and formed a functionalized wall surface portion. Then, T-cells engineered to express a T-cell receptor against an antigen presented on the tumour cell line (fluorescently stained in red) or non-engineered T-cells without specificity towards the tumour cell line (fluorescently stained in green) were infused and the chip was incubated for 30 minutes at 37° C. to allow T-cell—tumour cell binding to occur. FIG. 7A shows an image of the T-cells in the sample holder. The specific (red stained) cells are here shown in light grey, and the non-specific cells (green stained) are shown in darker grey. The signals of the respective cells are separately shown in FIG. 7B (red stained/specific) and FIG. 7C (green stained/non-specific), for comparison and clarity. To subsequently select and isolate specifically bound T-cells, an acoustic wave was generated in the sample holder, providing acoustic forces. T-cells that were not bound or weakly bound to the tumor cells were acoustically levitated by the acoustic force towards acoustic nodes, located c.a. 20 µm above the tumor cells (compare FIGS. 3A-3D). Because of mode-mixing between axial and lateral normal modes of the acoustic cavity, in the sample holder acoustic nodes not only formed in the axial direction but in the lateral directions as well. As a result, unbound levitated T-cells tended to aggregate in lines formed by the combination of the axial and lateral nodes. In FIG. 8A these appear as discrete horizontal bands, whereas the bound cells remain substantially in place, best visible from a comparison of FIG. 8A, and FIGS. 8B and 8C showing, respectively, all cells and, for comparison and clarity, individually the different specific and non-specific cells (cf. FIGS. 7A-7C). The lateral acoustic node structures which causes the aggregation of unbound cells into lines makes detection of the unbound cells more easy and may enhance of the visibility of the cells, in particular with respect to the bound cells. It should be clear that such structuring is not essential for detection of the unbound state per se or for the ability to sort cells based on avidity. E.g., distinguishing between the bound or unbound states can also be done based on tracking of axial motion and/or lateral motion of the cells without lateral node structure.

Note that complex acoustic force fields with plural nodes may also be generated by plural acoustic wave generators connected with the sample holder to generate acoustic waves in the holding space from perpendicular directions, which generators may be separately controllable and may provide non-stationary force fields, e.g. inducing movement of (groups of) cells in moving acoustic nodes.

Figure 9A:
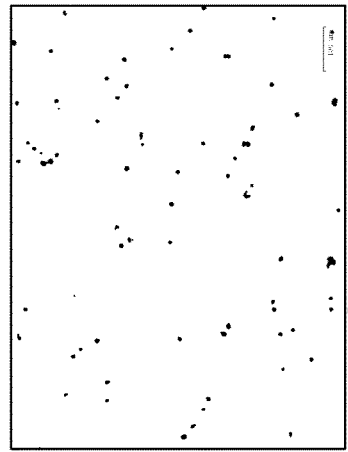
Figure 7B:
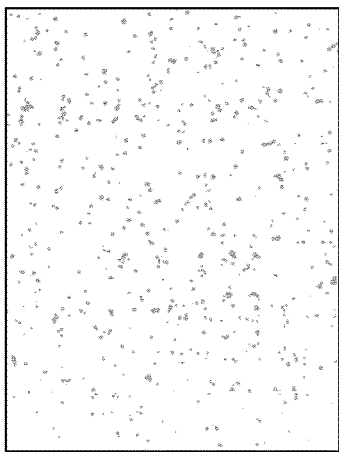
Figure 8B:
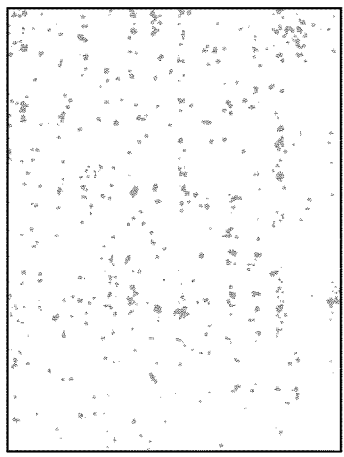
Figure 9B:
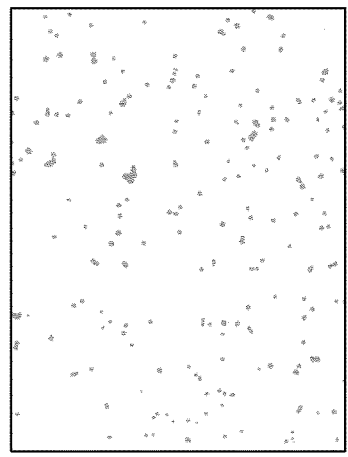
Figure 7C:
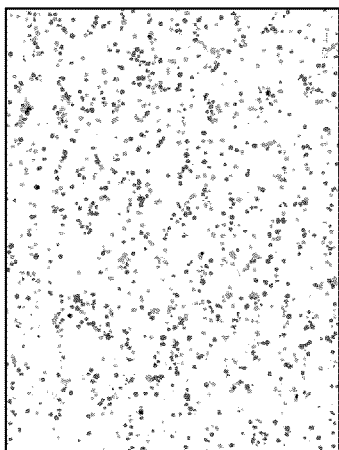
Figure 8C:
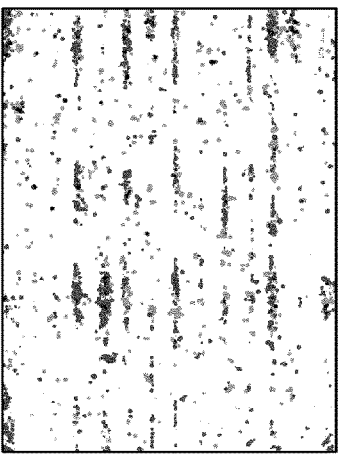
Figure 9C:
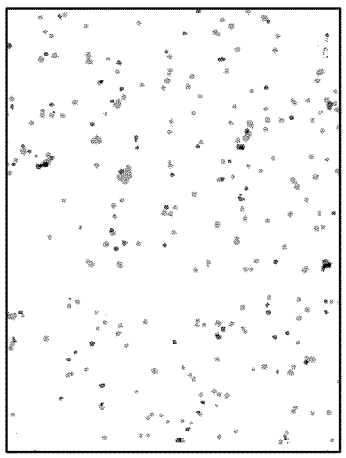
Figure 10:
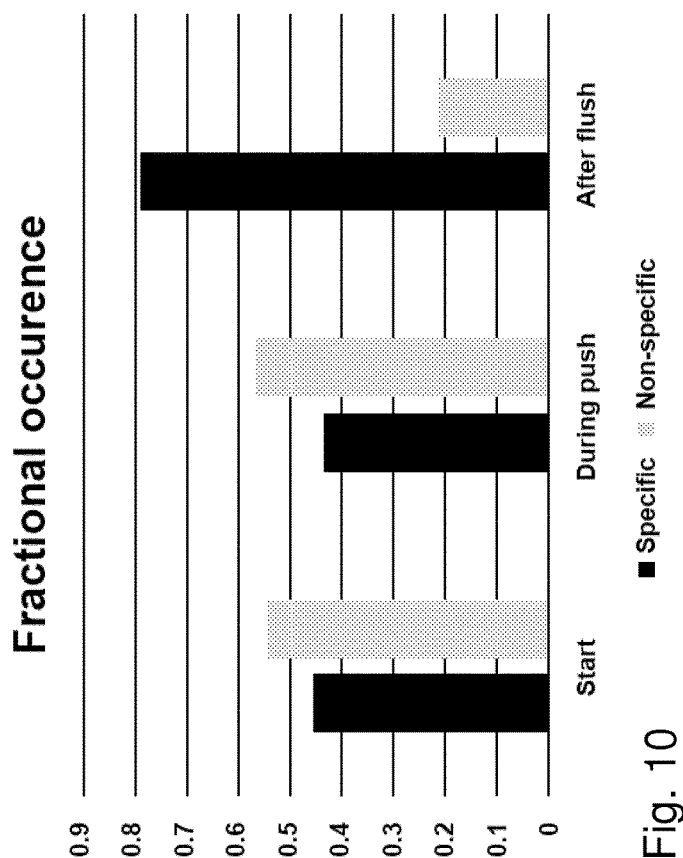
FIG. 10 depicts a summary result of experimental tests.

In a subsequent step, gentle flushing of the sample space, e.g. by flowing sample fluid through it, removed the unbound cells causing a relative enrichment of the specific T-cell population in the sample space, see FIGS. 9A-9C indicating like FIGS. 7A-7C and 8A-8C the remaining cells (FIG. 9A: all cells, FIGS. 9B-9C the different specific and non-specific cells individually). FIG. 10 shows the fractional occurrence (relative fraction of total cell count) of specific and non-specific cells in the field-of-view for the three steps shown in FIGS. 7A, 8A, 9A.

Figure 11:
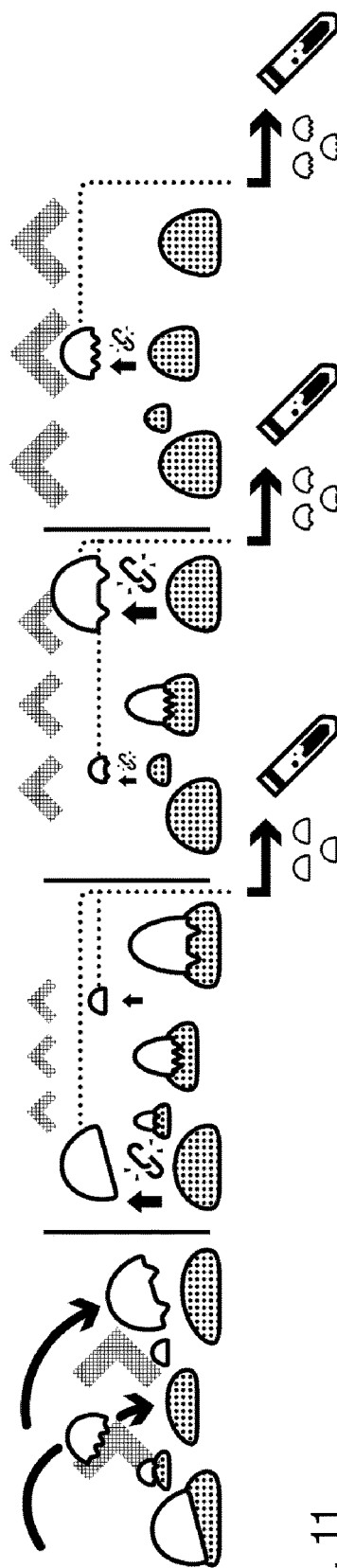
FIG. 11 indicates another method of studying interaction kinetics on cellular bodies by acoustic waves in the holding space.

Repeating such protocol (incubation, application of acoustic wave, flushing; optional further incubation, application of acoustic wave, flushing; repeat as desired) at increasing levels of applied acoustic forces allows to screen and collect T-cells based on their tumor cell avidity. This sorting process is illustrated in cartoon-style in FIG. 11 (compare also (the discussion of) FIGS. 4A-4C). FIG. 11 indicates from left to right: introduction of T-cells (indicates as half spheres) with target moieties (indicated as "legs" on the cells) and incubation; application of weak acoustic wave (indicated with thin symbols """) and lift-off of unbound cells (broken link); flushing and collection of unbound cells in a vial; application of moderately strong acoustic wave (indicated with medium heavy-printed symbols """) and lift-off of weakly bound cells (broken links); flushing and collection of detached weakly bound cells in a vial; application of strong acoustic wave (indicated with heavy printed symbols """) and lift-off of strongly bound cells (broken link); flushing and collection of detached strongly bound cells in a vial.

In a therapeutic setting, one or more of the thus isolated T-cell fractions may then be selected for administration to a recipient for treatment, in particular for treatment of the patient from whom the studied target tumor cells were harvested. The same principles of avidity based cell screening and/or selection for therapy and/or research can also be applied to fundamental research in immunology and/or cell biology, to study other forms of avidity based cell applications, and use therein, such as immune therapies which may include immune suppression therapies for patients having received a donor organ.

The disclosure is not restricted to the above described embodiments which can be varied in a number of ways within the scope of the claims as explained supra.

Elements and aspects discussed for or in relation with a particular embodiment of the method or system may be suitably combined with elements and aspects of other embodiments of the system or method, unless explicitly stated otherwise.

The invention claimed is:

1. A method of manipulating and/or investigating cellular bodies, comprising steps of:
providing a sample holder comprising a holding space for holding a fluid medium;
providing the holding space with a functionalised wall surface portion to be contacted by a sample, wherein the functionalised wall surface portion comprises one or more of biological tissue portions, cells, and tissues; and
providing the sample comprising one or more cellular bodies in a fluid medium in the holding space, whereby the sample is in contact with the functionalised wall surface portion;
exerting a force on the one or more cellular bodies of the sample in the holding space,
determining a relation between the force and an adhesion strength and/or adhesion kinetics of one or more of the cellular bodies to the functionalised wall surface portion, and/or
sorting and/or collecting at least part of the cellular bodies on the basis of a relation between the force and an adhesion strength and/or adhesion kinetics of the one or more of the cellular bodies to the functionalised wall surface portion.

2. The method of claim 1, comprising at least one of introducing a sample fluid containing one or more cellular bodies into the holding space and/or removing the sample fluid from the holding space.

3. The method of claim 1, wherein the functionalised wall surface portion is further provided with one or more primers which may comprise one or more types of interaction moieties selected from at least one of antibodies, peptides, biological tissue factors, bacteria, antigens, proteins, ligands, viruses, drug compounds, lipid (bi)layers, fibronectin, cellulose, nucleic acids, RNA, small molecules, allosteric modulators, biofilms, "organ-on-a-chip", and atomic or molecular surface portions to which at least part of the sample tends to adhere with preference relative to other surface portions of the holding space.

4. The method of claim 1, comprising a step of detecting and/or monitoring at least one property of at least one of the cellular bodies
wherein the at least one property comprises, or is, at least one of: cell integrity, adhesion of a cellular body to at least part of the functionalised wall surface portion, motion of at least one of the cellular bodies, fluorescence emission, viability signs of at least one of the cellular bodies, and wherein the step of detecting and/or monitoring comprises at least one of:

optical detection; and acoustic detection.

5. The method of claim 1, comprising at least one of:

tracking motion of one or more cellular bodies as a function of monitoring an optical activity of one or more of the cellular bodies;

varying a temperature and/or a temperature profile of the sample holder; and varying an illumination and/or illumination profile of the sample holder.

6. The method of claim 2, comprising at least one of:

tracking motion of one or more cellular bodies as a function of at least one of a flow of sample fluid and a composition of sample fluid; and varying a composition of the sample fluid.

7. The method of claim 1, further comprising the step of quantifying an adhesion strength between at least one of the cellular bodies and a functionalized surface portion.

8. The method of claim 1, wherein the cellular bodies are devoid of microbeads and/or magnets.

9. The method of claim 1, wherein at least a portion of the cellular bodies are provided with chromophores and/or fluorescent staining.

10. The method of claim 1, wherein the method comprises generating an acoustic wave in the holding space exerting a force on the one or more cellular bodies of the sample in the holding space.

11. The method of claim 10, wherein the method comprises generating an acoustic wave in the holding space to exert the force on the one or more cellular bodies of the sample in the holding space, wherein the force is in a direction away from the functionalised wall surface portion.

12. The method of claim 10, comprising varying at least one of one of frequency and amplitude of the acoustic wave in the holding space.

13. The method of claim 1, wherein the functionalised layer and/or the cellular bodies comprise one or more of tumor cells, immune cells, T-cells, and B-cells.

14. The method of claim 1, comprising removing at least part of the cellular bodies from the holding space after the sample has contacted the functionalised wall surface portion and further analysing the at least part of the cellular bodies that were removed from the holding space with one or more other methods selected from single-cell sequencing, fluorescence microscopy, and cryo-electron microscopy.

15. The method of claim 1, comprising obtaining from a subject at least one of the cellular bodies and the one or more of biological tissue portions, cells, and tissues of the functionalised wall surface portion.

16. The method of claim 15, further comprising removing at least part of the cellular bodies from the holding space after the sample containing the cellular bodies has contacted the functionalised wall surface portion and administering the at least part of the cellular bodies to another subject and/or to the original subject.

\* \* \* \* \*